(12) United States Patent
Wilcox

(10) Patent No.: US 11,052,024 B2
(45) Date of Patent: Jul. 6, 2021

(54) FEEDING SYSTEM FOR GASTRIC TUBE PATIENTS

(71) Applicant: Clinton Wilcox, Grass Valley, CA (US)

(72) Inventor: Clinton Wilcox, Grass Valley, CA (US)

( * ) Notice: Subject to any disclaimer, the term of this patent is extended or adjusted under 35 U.S.C. 154(b) by 0 days.

(21) Appl. No.: 16/516,517

(22) Filed: Jul. 19, 2019

(65) Prior Publication Data

US 2020/0022878 A1 Jan. 23, 2020

Related U.S. Application Data

(60) Provisional application No. 62/700,471, filed on Jul. 19, 2018.

(51) Int. Cl.
*A61J 15/00* (2006.01)

(52) U.S. Cl.
CPC ....... *A61J 15/0015* (2013.01); *A61J 15/0076* (2015.05); *A61J 15/0088* (2015.05); *A61J 15/0092* (2013.01); *A61J 15/0003* (2013.01); *A61M 2210/1053* (2013.01)

(58) Field of Classification Search
CPC ............. A61J 15/0015; A61J 15/0076; A61J 15/0092; F04B 33/00; F04B 417/555; A61M 39/08; A61M 39/22
See application file for complete search history.

(56) References Cited

U.S. PATENT DOCUMENTS

| | | | | |
|---|---|---|---|---|
| 2,657,834 A | * | 11/1953 | Flavius | B05B 11/3049 222/321.9 |
| 4,950,254 A | * | 8/1990 | Andersen | A61J 15/0026 604/213 |
| 5,372,578 A | | 12/1994 | Kriesel et al. | |
| 2004/0153047 A1 | * | 8/2004 | Blank | B65D 5/746 604/408 |
| 2007/0276356 A1 | | 11/2007 | Downing et al. | |
| 2008/0103475 A1 | * | 5/2008 | Hendricks | A61J 15/0096 604/403 |
| 2008/0195047 A1 | * | 8/2008 | Price | A61J 15/0092 604/151 |
| 2008/0319391 A1 | * | 12/2008 | Jackson | A61J 15/0076 604/142 |
| 2016/0194113 A1 | * | 7/2016 | Aquino | A47G 23/032 220/737 |

FOREIGN PATENT DOCUMENTS

JP 2013022157 A 2/2013

* cited by examiner

*Primary Examiner* — Rebecca E Eisenberg
*Assistant Examiner* — John A Doubrava
(74) *Attorney, Agent, or Firm* — Temmerman Law; Mathew J. Temmerman

(57) ABSTRACT

A feeding system for medical patients comprises a storage assembly, dispensing assembly, and extension set including, in part, a reservoir, a pump, a feeding tube, a check valve and an adapter. The reservoir is configured to hold at least one feeding of nutritional substance. The dispensing assembly is connected to the storage assembly and pumps the at least one feeding of nutritional substance from the reservoir to the feeding tube connected to an outlet of the pump. The check valve unit is connected to a second end of the feeding tube by means of a check valve connection point and is configured to allow the flow of nutritional substance in only one direction. The at least one feeding of nutritional substance is passed through the adapter unit connected to the check valve unit.

7 Claims, 11 Drawing Sheets

FEEDING SYSTEM FOR GASTRIC TUBE PATIENTS

This application claims priority from the United States provisional application having Ser. No. 62/700,471, filed Jul. 19, 2018. The disclosure of that provisional application is incorporated herein by reference as if set out in full.

BACKGROUND OF THE DISCLOSURE

Technical Field of the Disclosure

This invention relates generally to the field of medical feeding systems, and more particularly to a medical feeding system having a feeding tube which is portable, easy to operate, and does not require the multiple reloading of syringes and other feeding system elements.

Description of the Related Art

There are variety of medical conditions wherein a patient is no longer able to swallow normally including throat cancer, head trauma, disease or abnormalities of the gastrointestinal tract metabolic disorders, and many other conditions. Often the ability to swallow is lost. In other instances, the act of swallowing sends food or liquid into the lungs instead of the stomach. This can result in a decline in general health, loss of weight, and other ailments. In these situations, a patient may require the use of a feeding tube in order to meet his or her caloric requirements. In many cases, the requirement for use of a feeding tube is a lifelong necessity and a patient must learn to feed himself or herself independently.

Systems, devices and methods currently exist for providing flowable nutritional substance (e.g., formula, liquid food, liquid medicine, etc.) to a patient who is unable to ingest food normally. Such systems, devices and methods generally fall within one of two broad categories: intravenous (IV) delivery or enteral delivery.

In traditional hospital settings, both IV delivery and enteral delivery systems commonly employ a gravity-based bag method. The gravity-based bag method is also referred to herein as the "bag method". Typically, the patient using this method must remain substantially immobile, thereby making it is feasible to suspend a bag of flowable nutritional substance above him or her. This arrangement utilizes gravitational force to dispense nutritional substance to a patient. As a result, the delivery rate is relatively constant. Accordingly, the user has little to no influence on the flow rate. The user may squeeze the bag to increase the flow rate, but this approach requires the application of a significant force on the part of the user. In addition, the bag must be maintained above the point of delivery, which reduces the convenience of such a system to the user. Furthermore, as the nutritional substance is delivered to the stomach, the pressure within the stomach increases. The increased pressure slows, and can even stop, the delivery of nutritional substance from the bag.

In out-of-hospital settings, gravity bolus feeding systems represent the primary feeding tube systems utilized by patients. Typically, gravity bolus feeding systems utilize a syringe barrel. To control the rate of feeding, the syringe barrel is raised or lowered by hand. In use, the open tube allows air and stomach contents to express back into the syringe barrel via a process referred to as "venting".

Similar to the bag method, gravity bolus feeding systems suffer from several disadvantages. The disadvantages of syringe feeding include the fact that: a) a user must mix the nutritional substance in a separate reservoir and draw the nutritional substance into the syringe, b) a user must hold the syringe barrel for an extended period of time (typically 20 to 40 min) required for a feeding, c) once the feeding is started, it is difficult to interrupt or stop, d) when venting occurs, the contents of the syringe barrel are often splashed out of the open top, e) the typical syringe barrel only holds 60 cubic centimeters of liquid food, much less than the average of approximately 200 cubic centimeters that a majority of adults require for an entire feeding, and f) the user must generally plunge and pull the syringe several times to feed and reload the syringe during a single feeding.

Moreover, the user is required to apply a significant force to actuate the syringe plunger, in some cases leading to breakage of feeding system components and/or the formation of microtears in the syringe plunger. Broken components and microtears can lead to leakage of the feeding system, in addition to the establishment of bacterial plaques posing a health hazard to a patient. Finally, both this large force requirement and the above-mentioned small feeding volumes often mean that actuation of the syringe plunger (and re-loading of the syringe 32) is difficult for some patients. For some patients, such as those with smaller hands or weaker grips, the act of spreading the fingers and thumb far enough to grip a full syringe may require multiple trips in and out of the feeding tube. Thus, such patients may require assistance by one or more helpers.

Therefore, standard medical feeding systems in general, and enteral feeding systems specifically, leave a great deal to be desired for the purposes of convenience and safety. There is a need for a feeding system that efficiently and safely delivers nutritional substance to a patient who cannot ingest food normally. Such a needed system would hold sufficient food volume for an entire feeding and thereby eliminate the need to re-use syringes multiple times. Further, as the feeding system would hold sufficient nutritional substance for the entire feeding, the system would need to be connected to the existing feeding tube port only once, which would not only reduce the chance for infection, but would also reduce the wear and tear in the feeding system. In turn, this would greatly increase the lifespan of the feeding tube and the feeding system. Such a system would be easy to operate and could be easily cleaned, further enhancing the safety of the feeding system. Such a system would optionally allow medication to be added to the feeding system. Such a feeding system would allow the patient to completely feed themselves, and to do so at an increased rate relative to conventional systems. This would in turn increase the health of the patient because they would be more likely to feed. Such a system would provide an easy means for feeding the patient in travel. Moreover, the system would minimize the chance of transmitting air into the patient's stomach. The present embodiment overcomes shortcomings in this area by accomplishing these critical objectives.

SUMMARY OF THE DISCLOSURE

In order to minimize the limitations found in the existing systems and methods, and to minimize other limitations that will be apparent upon the reading of this specification, the preferred embodiment of the present invention provides a feeding system that allows a user to deliver food, water and other liquids to the patient's abdomen through an existing feeding tube.

In order to minimize the limitations found in the existing systems and methods, and to minimize other limitations that will be apparent upon the reading of this specification, the preferred embodiment of the present invention provides a feeding system that allows a user to deliver food to the patient's abdomen through an existing feeding tube.

In its preferred embodiment, the feeding system comprises a storage assembly, a dispensing assembly and an extension set. The storage assembly includes a body member, the body member having a reservoir with a delivery end, a bottom end, and an outer wall. The outer wall incorporates a one-way port that permits a pressurizing nutritional substance to enter the reservoir. The body member further comprises a cap that is securable to a reservoir opening of the reservoir, the cap and said reservoir opening configured to create an enclosed reservoir. The dispensing assembly is a manual dispensing assembly comprising a pump with an actuator head and an actuator outlet, the actuator head being depressed in response to a user applying a downward force on the actuator head during a dispensing stroke. The actuator outlet is attached to a first end of the feeding tube. The extension set includes a check valve unit operably connected to a second end of the feeding tube and an adapter unit operatively attached to the check valve unit. The adapter unit connects to a feeding tube port attached to the patient's abdomen. The dispensing assembly may also include an electric pump. Further, the one-way port may be adapted to reversibly attach to the second end of the feeding tube in order to stow the feeding tube when it is not in use. Further, the adapter unit comprises a male screw type adapter, the male screw type adapter further configured to engage a female end cap. In addition, the female end cap is further configured to reversibly engage the port.

In addition, the feeding system comprises a reservoir configured to hold at least one feeding of nutritional substance. Nutritional substance may include at least one full dose or entire feeding of flowable food, water and/or medication. During a dispensing stroke, the reservoir, pump, and feeding tube operatively engage to draw nutritional substance from the reservoir to the feeding tube through the outlet. Nutritional substance, comprising flowable food, medicine and the like, is filled into the reservoir through a reservoir opening. Nutritional substance filled through the reservoir opening of the port may be referred to as nutritional substance, while nutritional substance fed into the reservoir through a one-way valve of the port or another pressurizing source may be referred to as "pressurizing nutritional substance". The pump is connected to the reservoir and is configured to pump the at least one food item in the reservoir to the abdomen of the patient. The pump includes an actuator, a delivery tube, a cap and a housing having a spring and a steel ball which is attached to a dip tube. The actuator includes an outlet to which the feeding tube of the feeding system is attached. The actuator is connected to the delivery tube and the cap. The cap of the pump engages with the reservoir opening to form an enclosed reservoir. The dip tube is notched at the distal end to allow all possible food/liquid to be depleted, and includes a proximal end which is attached to the spring and a distal end which acts as an inlet of the pump. The feeding tube includes a first end attached to the actuator outlet and a second end being attachable to the feeding tube port. The first end of the feeding tube is connected to the outlet of the actuator and the second end is connected to the check valve of an extension set. The check valve is configured to allow the flow of the food item in only one direction. The one-way check valve prevents the food item from returning out from the patient and also prevents the nutritional substance remaining in the tube from moving backwards. The adapter is connected to the check valve by means of a connection point. The adapter is configured to allow the passage of the at least one food item into an existing feeding tube port connected to the patient's abdomen. Through the feeding tube port, the food enters into the abdomen of the patient with the help of the feeding system of the present invention. The adapter is a male screw type adapter that can be easily connected via several adapter choices to the feeding tube port connected to the patient's abdomen. When the actuator of the pump is pressed by the user, the pump pumps the at least one food item or water contained in the reservoir through the feeding tube to the adapter and to the abdomen of the patient. After use, the patient may flush the system with water.

A first objective of the present embodiment is to provide a feeding system that provides nutrition to a patient who cannot swallow food safely.

A second objective of the present embodiment is to provide a feeding system to the patient who is unable to obtain nutrition by mouth and that allows foods to be inserted into the patient's digestive tract directly.

A third objective of the present embodiment is to provide a system that holds sufficient food quantity for an entire feeding and thereby eliminates the need to re-use syringes multiple times during use.

A fourth objective of the present embodiment is to provide a feeding system that does not need to be connected to the existing feeding tube port more than one time during a feeding, thereby maintaining a clean, hygienic system that reduces the chance of infection, reduces wear and tear on the system components, and increases the lifespan of the feeding tube.

A fifth objective of the present embodiment is to provide a feeding system that is portable, lightweight, easy to operate, and easily cleaned, can be stored easily for repeated use.

Another objective of the present embodiment is to provide a feeding system that due to the advantages described here, allows the patient to completely feed on their own much faster which increases the health of the patient and decreases the likelihood that the patient skips feedings.

Yet another objective of the present embodiment is to provide a feeding system that provides an easy means for feeding the patient in travel, including components which are light, flexible, easily transportable, and adaptable to provide use of the feeding system while transporting.

Still another objective of the present embodiment is to provide a feeding system that minimizes or prevents any air going into the patient's stomach.

In addition, one or more preferred embodiments are simple in construction so as to be relatively inexpensive to manufacture.

These and other advantages and features of the present invention are described with specificity so as to make the present invention understandable to one of ordinary skill in the art.

BRIEF DESCRIPTION OF THE DRAWINGS

Elements in the figures have not necessarily been drawn to scale in order to enhance their clarity and improve understanding of these various elements and embodiments of the invention. Furthermore, elements that are known to be common and well understood to those in the industry are not depicted in order to provide a clear view of the various embodiments of the invention, thus the drawings are generalized in form in the interest of clarity and conciseness. These and other features, aspects, and advantages of the present invention are described below with reference to preferred embodiments. The preferred embodiments of the invention are intended to illustrate, but not to limit the present invention. The drawings contain seven figures.

DETAILED DESCRIPTION OF THE DRAWINGS

Figure 1:
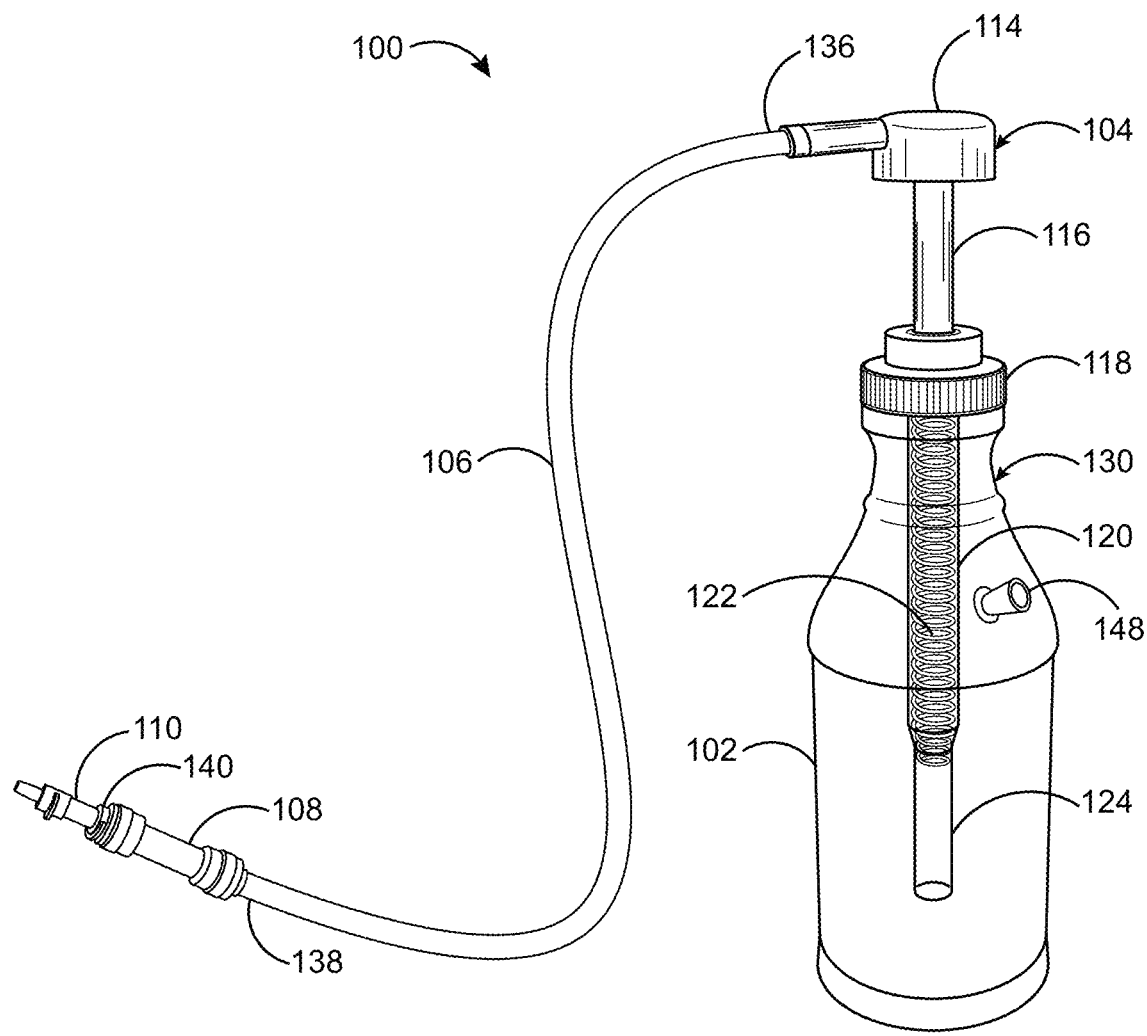
FIG. 1 illustrates a perspective view of a feeding system for medical patients in accordance with the preferred embodiment of the present invention.

In the following discussion that addresses a number of embodiments and applications of the present invention, reference is made to the accompanying drawings that form a part hereof, and in which is shown by way of illustration specific embodiments in which the invention may be practiced. It is to be understood that other embodiments may be utilized and changes may be made without departing from the scope of the present invention. Furthermore, various applications of the inventions, and modifications thereto, which will be apparent to those who are skilled in the art, are also contemplated. For example, while the preferred embodiments are particularly useful in the context of enteral feeding, the systems, devices or methods may be useful in other applications as well, including a wide variety of dispensing applications for flowable substances.

Various inventive features are described below that can each be used independently of one another or in combination with other features. However, any single inventive feature may not address any of the problems discussed above or may only address one of the problems discussed above. Further, one or more of the problems discussed above may not be fully addressed by any of the features described below.

The present disclosure relates to systems and methods for delivering nutritional substance to a feeding tube. As used herein, the singular forms "a", "an" and "the" include plural referents unless the context clearly dictates otherwise. "And" as used herein is interchangeably used with "or" unless expressly stated otherwise. As used herein, the term "'about" means+/−5% of the recited parameter. All embodiments of any aspect of the invention can be used in combination, unless the context clearly dictates otherwise.

Unless the context clearly requires otherwise, throughout the description and the claims, the words "comprise", "comprising", and the like are to be construed in an inclusive sense as opposed to an exclusive or exhaustive sense; that is to say, in the sense of "including, but not limited to". Words using the singular or plural number also include the plural and singular number, respectively. Additionally, the words "herein", "wherein", "whereas", "above", and "below" and words of similar import, when used in this application, shall refer to this application as a whole and not to any particular portions of the application. Advantageously, the nutritional substance may be mixed, if necessary, after being added to the medical feeding device 90. The term "nutritional substance" is user herein in its ordinary meaning and is intended to refer generally to a flowable substance that is suitable for administration to the gastrointestinal (GI) system of a human or non-human animal. Although such a nutritional substance will often contain caloric substances, the term is also intended to cover non-caloric substances as well, such as medicine or water, for example, unless otherwise indicated. The term "nutritional substance" is used interchangeably with "food item", "flowable nutrient", "medicine", and "medicine mixed with food".

Referring to FIGS. 1A-5, a feeding system 100 for medical patients in accordance with the present invention is illustrated. The feeding system 100 is capable of receiving a nutritional substance, or other flowable substance, and delivering said flowable substance to the patient's stomach through an existing feeding tube port 150 (see FIG. 16). In one arrangement, a user may self-administer the nutritional substance using the system. In other arrangements, a user of the system may be administering a nutritional substance to another person or to a non-human animal. The term "user" is used in its ordinary meaning throughout the present disclosure and is intended to refer to a person interacting with at least a portion of the system to administer a nutritional substance to himself or herself, or to another person or non-human animal. The term "user" may also refer to a person or non-human animal that receives the nutritional substance through administration by another. Notably, "feeding system" is used interchangeably with "medical feeding system" herein. Also, "slide" is used interchangeably with "compress", "compressible", "deform" and "depress". In addition, the term "dispense" is used interchangeably with "expel".

In a general form of the present invention, the feeding system 100 includes a storage assembly 101, a dispensing assembly 103, and an extension set 137.

Figure 16:
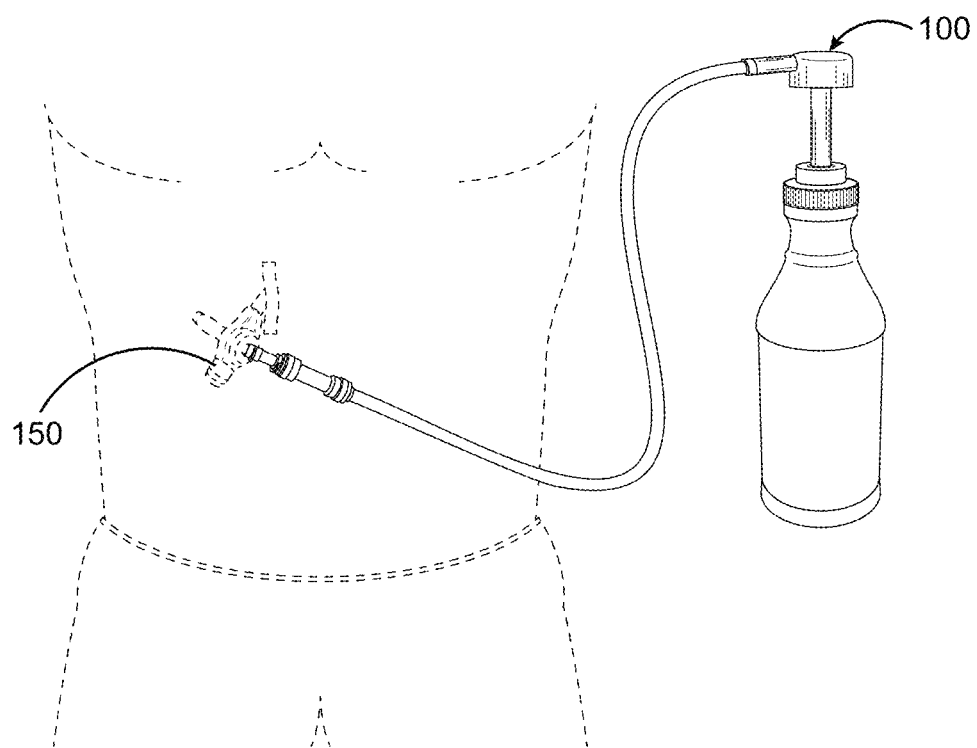
FIG. 16 illustrates a perspective view of the feeding system for medical patients in use in accordance with the preferred embodiment of the present invention.

In a specific form of the present invention, the storage assembly 101 includes a reservoir 102 and a port 148. Further, the dispensing assembly 103 includes a pump 104 and a body member 90. The pump 104 includes an actuator outlet 114 and a delivery tube 116. The body member 90 includes a cap 118, a spring assembly, and a dip tube 124. Finally, the extension set 137 includes a feeding tube 106 and a check valve unit 139 with an adapter 110 and a check valve connection point 140. As shown in FIG. 16, the feeding tube 106 extends from a location external of the body of the user to a feeding tube port 150 attached to a patient's stomach.

Figure 4:
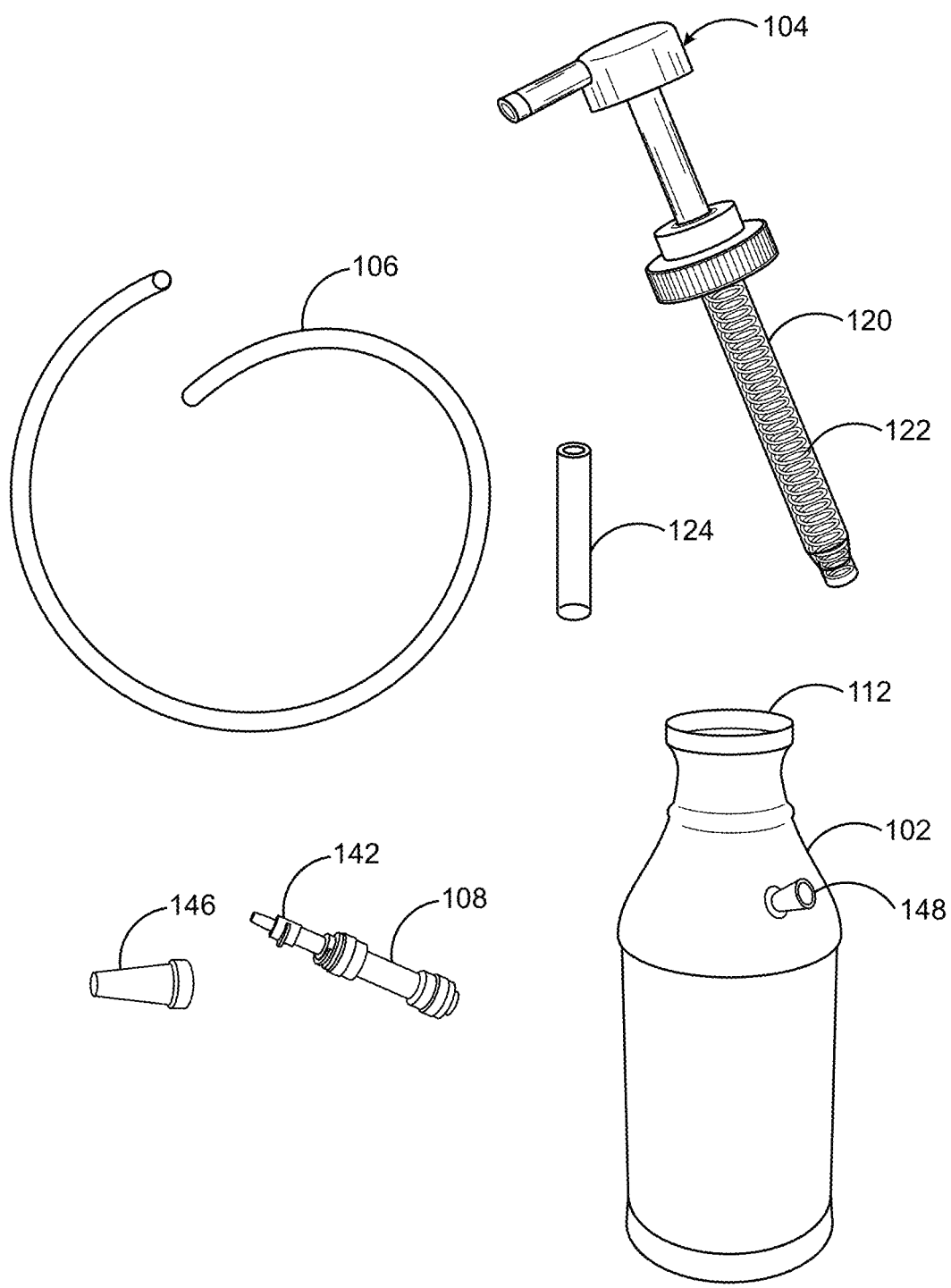
FIG. 4 illustrates an exploded view of the feeding system in accordance with the preferred embodiment of the present invention.

With reference to FIGS. 1A & 4, the storage assembly 101 includes a cup-like reservoir 102 having a delivery end 127 with a reservoir opening 112, a bottom end 129, and an outer wall 113 containing a port 148. The bottom end 129 of the reservoir 102 is substantially closed and includes a support base that is substantially flat. The outer-wall 113 of the reservoir 102 is disposed between delivery end 127 and the bottom end 129 of the reservoir 102. In some embodiments, the reservoir opening 112 is threadably engaged to a cap 118 of the manual dispensing assembly 103, wherein the reservoir 102 and the cap 118 engage to form an enclosed reservoir 130. Preferably, the thread between reservoir and cap are unique to the instant system. This unique "lock and key" approach means the threads of the cap are specifically designed to match only with the threads of the bottle, thus preventing the attachments of other bottles, thus maintaining cleanliness and accuracy of delivery. The bottle also contains graduations to ensure accuracy. In other embodiments, the cap 118 may engage the reservoir opening 112 in a different manner, such as a snap-fit arrangement or a screw-type closure similar to those commonly utilized on condiment bottles. In still further embodiments, the cap is widened beyond the width of the neck of the bottle, thereby creating a finger perch around which the user may hook his or her fingers to prove support for one handed pumping action.

In operation, the enclosed reservoir 130 is substantially leakproof, preventing leakage when the feeding system 100 is not upright. Also, the feeding system 100 remains leakproof when a patient burps or otherwise expels stomach contents back into the feeding device. In the preferred embodiment, the feeding system 100 only needs to be connected to the existing feeding tube port 150 once for the entire feeding as shown in FIG. 16. A single connection and disconnection reduces wear and tear on the feeding system 100, which in turn greatly increases the life of the feeding system 100. Relatedly, the reservoir 102 is sized to hold a volume of nutritional substance that is satisfactory for a single average feeding session without the need to switch out syringes or other medical feeding system 100 elements. On average, one feeding of nutritional substance can fall within the range of 8-16 ounces of flowable nutritional substance. Correspondingly, the feeding device may hold up to about 16 ounces in some embodiments. As mentioned above, the reservoir 102 is also configured to hold and dispense fluid medication to a patient. Said medication may be pre-mixed with flowable food items, solubilized in a fluid, or the like.

Figure 6A:
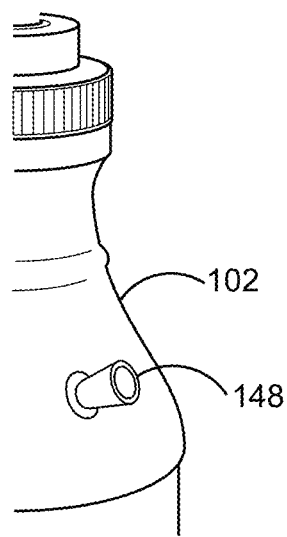
FIG. 6A illustrates a perspective view of a port on the reservoir of the feeding system in accordance with the preferred embodiment of the present invention.

FIG. 6A shows a port 148 integrated into the outer wall 113 of the reservoir 102 is a one-way leakproof pass-through from the reservoir 102. As illustrated in FIG. 6A, the port 148, also referred to herein as a "one-way port", defines a one-way passage from the exterior of the reservoir 102 to the interior of the reservoir 102. In some embodiments, a one-way valve may inserted into the one-way port may comprise a duckbill-type valve or an elastomeric slit valve. While the illustrated one-way port 148 is integrated into the outer wall 113 of the reservoir 102, in other embodiments the port 148 may be located in another suitable location. In some arrangements, the illustrated port 148 is funneled; however, in other arrangements, the port 148 is configured to form a snap-fit arrangement or the like. In other embodiments, a variety of commercially available medication ports are capable of being selectively coupled to the reservoir 102 via the port 148 in order to deliver medicinal substances to the reservoir 102. For example, the port 148 is adaptable to connect to a Y-Port. Specifically, the Y-Port allows a patient to administer medication into the reservoir 102 through the port 148 with a syringe or a similar instrument without the need to disconnect the feeding tube 106 from the feeding tube port 150.

Figure 6B:
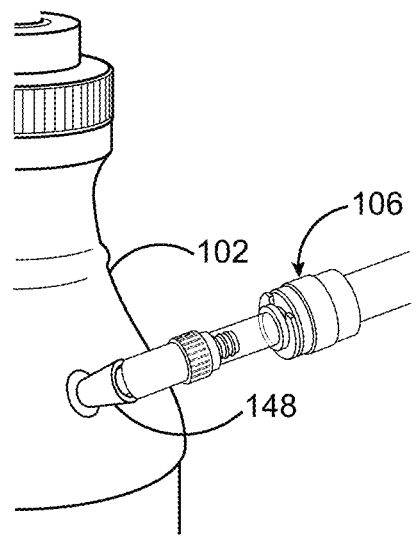
FIG. 6B illustrates a perspective view of the feeding tube stowed on the port of the feeding system when not in use in accordance with one embodiment of the present invention.

In operation, the one-way port 148 allows pressurizing nutritional substance to enter the reservoir 102. Pressurizing nutritional substance enters the reservoir 102 from the exterior of the reservoir through the port 148 to interior to the reservoir 102. The one-way valve of the port 148 also inhibits and preferably at least substantially prevents air and nutritional substance from the exiting the reservoir 102. An enclosed reservoir 130 is formed when the cap 118 is sealably engaged with reservoir opening 112. As shown in FIG. 6B, the one-way port 148 is also adapted to reversibly attach to the second end of the feeding tube 138 in order to stow the feeding tube 106 when it is not in use. Indeed, in the preferred embodiment the one-way port 148 is a convenient, sanitary place to stow the end of the feeding tube 106 when not in use.

Figure 3:
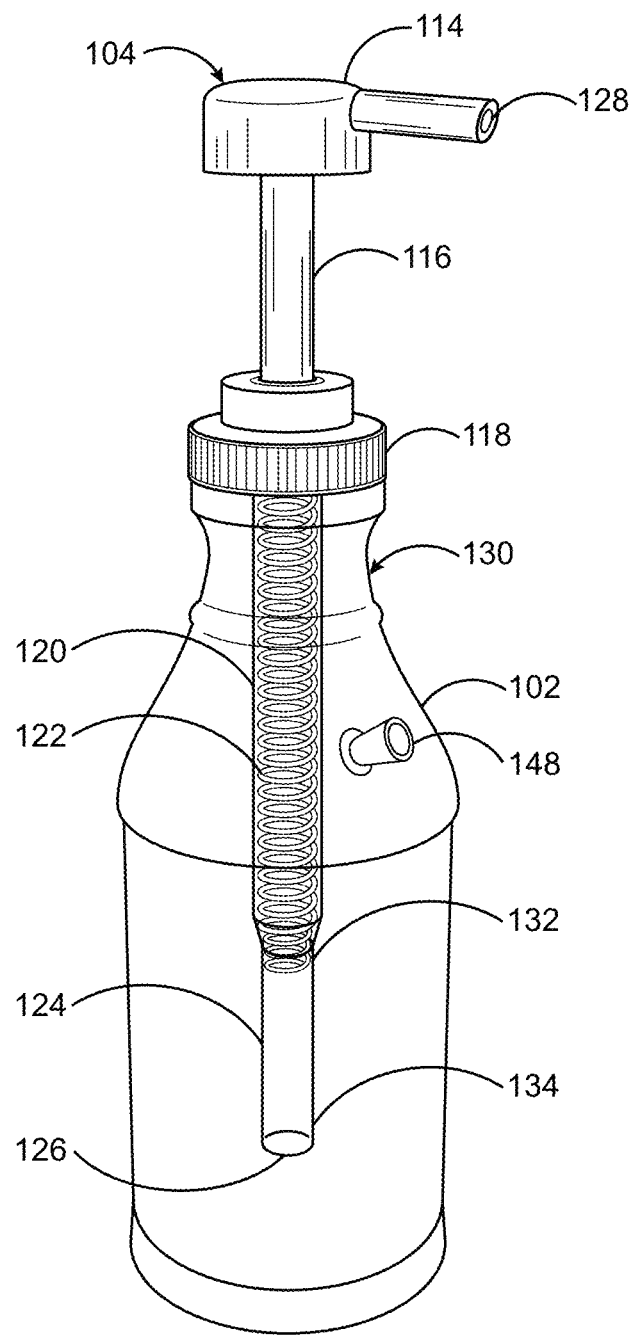
FIG. 3 illustrates a perspective view of the pump connected to a reservoir of the feeding system in accordance with the preferred embodiment of the present invention.

Referring to FIG. 1A, there is shown a storage assembly 101 and a dispensing assembly 103. In the preferred embodiment, the dispensing assembly 103 includes a pump 104, a body member 90, and an extension set 137. As illustrated in FIGS. 3 & 4, the body member 90 of the manual dispensing assembly 103 comprises a cap 118, a spring assembly, and a dip tube 124. The cap 118 of the body member 90 engages with the reservoir opening 112 to form an enclosed reservoir 130. In some embodiments, the cap 118 and the reservoir 102 are integrally connected.

In the preferred embodiment, the pump 104 is a standard pump that is made utilizing food and/or medical grade quality levels, and additionally using non-corrosive (cannot rust) metallic components. In some embodiments, the pump 104 of the dispensing assembly 103 is a manual pump 104. Notably, while a manual pump is illustrated in FIGS. 1A & 16, alternative pump types are contemplated in the present disclosure, including electric pumps, compressed gas pumps, hand bulbs, and the like. In other arrangements, the pump may comprise a hand bulb, push button, electric pump, a compressed gas pump, or the like.

As shown in FIG. 3, the pump 104 includes an actuator 114 having an actuator head 115 an actuator outlet 128, and a delivery tube 116. The actuator 114 is connected to the cap 118 through the delivery tube 116. The pump 104 of the dispensing assembly 103 is connected in fluid communication with the storage assembly 101. The spring assembly includes a housing 120 enclosing a spring 122 and a steel ball 304 (see FIG. 10).

The actuator 114 is attached to a first end of the feeding tube 136, and is adapted to move vertically with respect to the body member 90. In the preferred embodiment, the actuator 114 is spring biased upwardly by a spring of the spring assembly to rest at the upright position upon releasing the downward force applied by a user on the actuator head 115. The spring is custom sized to accommodate the typical strength of both children and adults.

In operation, when the actuator 114 of the manual pump is pressed by the user to provide a dispensing stroke, the pump 104 is urged to the depressed position by the downward force, thereby drawing nutritional substance into the reservoir 102 during the downstroke movement. The reservoir 102 is pressurized when fluid is drawn into the reservoir 102 by such a downstroke movement and, as actuation of the pump 104 is repeated, pressure within the reservoir 102 builds until nutritional substance is expelled through the actuator outlet 128 into the feeding tube 106 of a patient. In other embodiments, the manual force provided by a user may pressurize a chamber within the reservoir 102, or a similar cavity, rather than pressurizing the reservoir 102 itself. In yet another embodiment, said manual force may pressurize an air space within the feeding tube 106. In practice, a predetermined number of pumps is necessary to deliver a typical volume of 12 ounces. For instance, in a preferred embodiments, approximately 40 pumps delivers 12 ounces of fluid.

In use, the manually-actuated pump 104 is capable of pressurizing the storage assembly 101 using energy originating from the user. As a result, the feeding device may be used nearly anywhere without the need for an external source of power. In addition, the manually-actuated pump of the present invention is lightweight to enhance portability and is relatively simple to use. Further, the manually-actuated pump of the present invention also provides the user with a great deal of control over the delivery flow rate of the nutritional substance delivery. For example, a user may interrupt a feeding at any time and may increase the rate of feeding at will. In one embodiment, the application of manual force by a user occurs during delivery of the expelled nutritional substance to the feeding tube port 150.

Figure 2:
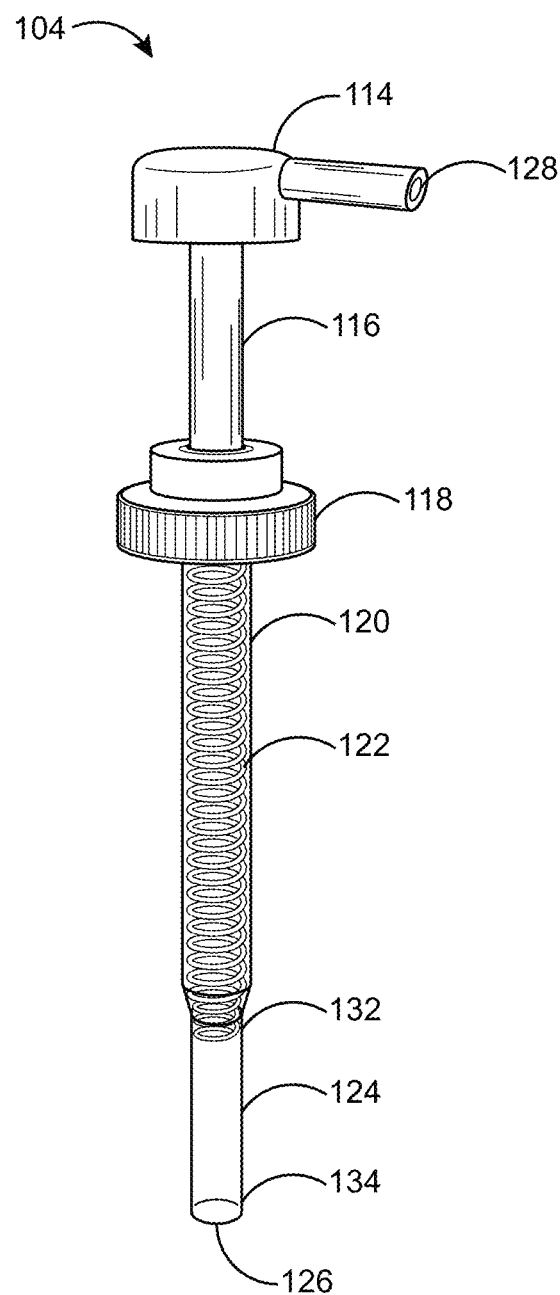
FIG. 2 illustrates a perspective view of a pump of the feeding system in accordance with the preferred embodiment of the present invention.

As shown in FIG. 2, the body member 90 and the pump 104 are operatively engaged during use of the feeding system 100. Advantageously, assembly and disassembly of the body member 90 and the pump 104 of the dispensing assembly 103 are very straightforward, thereby promoting patient self-feeding. As shown in FIG. 3, when operatively attached, the pump 104 and body member 90 of the manual dispensing assembly 103 are substantially leakproof, preventing or at least substantially reducing the incidence of spillage, contamination, and accidental and/or inadvertent release of the nutritional substance. An enclosed reservoir 102 is formed when the cap 118 of the body member 90 is engaged to the reservoir 102, thereby permitting a user to fill the reservoir 102 with pressurizing nutritional substance via the port 148.

In the preferred embodiment, the pressing of the actuator outlet 128 may be repeated at a user selected magnitude and frequency in order to further pressurize the reservoir 102 and cause the nutritional substance to be expelled from the reservoir 102 at a desired flow rate. Such an arrangement provides the ability for the user to select a desired flow rate for the nutritional substance from a wide variety of possible flow rates. In one embodiment, for example, a complete feeding of a 12 oz bolus can be completed in 5 minutes. Moreover, the flow rate can be easily, and even substantially, varied through the course of a single feeding. As a result, the user can substantially mimic the feed volume and flow rates that are achievable through oral feeding.

As illustrated in FIGS. 2A & 2B, the body member 90 includes a cap 118, a spring assembly, and a dip tube 124. In the preferred embodiment the spring assembly comprises a housing 120 having a spring 122 and a steel ball 304 (see FIG. 10) attached to a dip tube 124. The dip tube 124 includes a dip tube proximal end 132 which is attached to the spring 122 and a dip tube distal end 134 which acts as an inlet 126 of the pump 104. The dip tube proximal end 132 lies below the surface of the nutritional substance within the reservoir 102. During a dispensing stroke, nutritional substance from the reservoir 102 enters the body member 90 and the pump 104 via the nutritional substance inlet 36 of the dip tub.

The check valve unit 139 is configured to allow the flow of the food item in only one direction. Notably, the term "check valve" and "one-way check valve" are used interchangeably. The check valve unit 139 includes a check valve 108 and a check valve connection point 140, the check valve connection point 140 for operatively attaching the adapter 110 to the check valve 108. The check valve 108 of the check valve unit 139 prevents the flow of nutritional substance from a patient into the feeding tube 106. Further, the check valve 108 prevents flowable nutritional substance remaining in the feeding tube 106 from moving backwards into the reservoir 102. In some embodiments, the check valve may comprise a quarter turn valve that stops the flow of liquid. Any suitable check valve system may be utilized.

Figure 5:
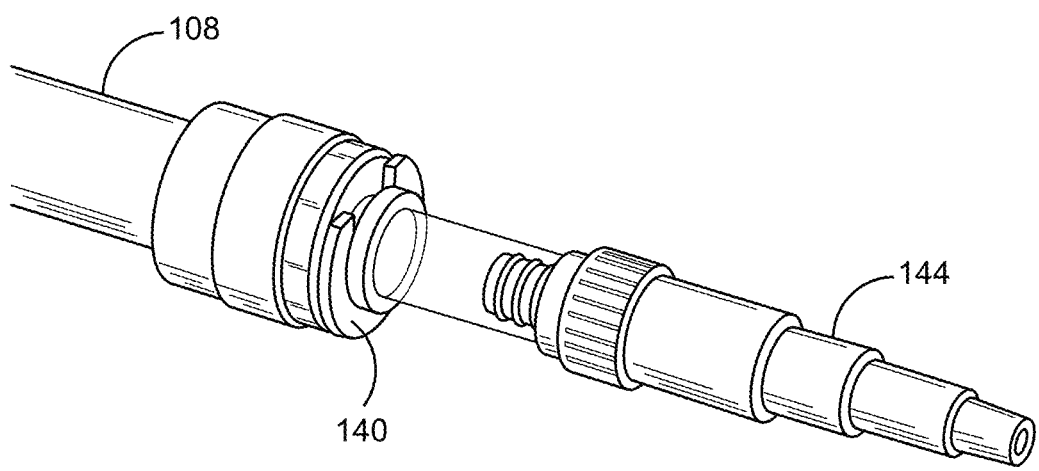
FIG. 5 illustrates a perspective view of an adapter connected to a feeding tube in accordance with one embodiment of the present invention.

The adapter unit is configured to allow the passage of the at least one food item into the existing feeding tube port 150 (see FIG. 16) connected to the patient's abdomen. As shown in FIGS. 1A & 4, the adapter unit includes an adapter 110 and an adapter end cap 146, the adapter 110 being connected to the check valve 108 by means of a check valve connection point 140. In some embodiments, the adapter 110 is a male screw type adapter 142 which can be easily connected to the feeding tube port 150 (see FIG. 16) connected to the patient's abdomen. In another embodiment, a low-profile G tube may be used, including those referred to as a Mic-Key by Halyard/Avanos, or those made by other manufactures such as AMT, Mini-One, Covidien, and Bard. These systems lock with a quarter turn, but the connection maintains a swivel for comfort and maneuverability. In other embodiments, a leakproof sealing fitting is used such as the silicon rubber ENFit® adapter 144 as shown in FIG. 5 may be used. In other embodiments, adapters are provided to allow the tubing to connect with legacy feeding tubes. Notably, said fittings are substantially leak-proof for all embodiments described herein. In other embodiments, a one quarter inch screw connector and graduated tip may be used for the connection to the feeding tube port 150.

In one embodiment, a female end cap 146 is employed for protection and to keep the feeding system 100 clean when not in use or when traveling. The female end cap 146 screws on to the male screw type adapter 142. If the ENFit® adapter 144 is used, then the female end cap 146 may not be suitable, and a compatible ENFit® cap 145 that accomplishes the same connection may be employed. These and other adapters may alone make the system compatible with nearly all feeding tube ports. Another use for the female end cap 146 is in the case where feeding is interrupted and the user temporarily places the cap 146 on the open tube to prevent food from flowing therethrough. As shown in FIG. 6B, in another embodiment the second end of the feeding tube 138 may also be configured to temporarily connect to the port 148 of the storage assembly 101 when feeding is interrupted and/or when the feeding system 100 not in use.

As illustrated in FIG. 16, the feeding tube 106 of the extension set 137 extends between the pump 104 of the manual dispensing assembly 103 and the feeding tube port 150. The feeding tube 106 may be made of a soft silicone rubber and includes a first end 136 and a second end 138. The first end 136 of the feeding tube 106 is connected to the outlet 128 of the actuator 114 and the second end 138 is connected to the check valve 108. In some embodiments, the feeding tube 106 may be constructed of relatively flexible materials, such as silicon, low density polyethylene, and other elastomeric materials. In another embodiment, the feeding tube 106 is constructed of soft silicone rubber. The type of material and/or thickness of the material for feeding tube 106 may also be selected based on whether the feeding tube 106 is intended to be reused, or if feeding tube 106 is intended to be disposable. In other embodiments, adapters are provided to allow the tubing to connect with legacy feeding tubes.

In some embodiments, one or more components of the feeding system 100 may define portions of both the reservoir 102 and the pump 104. For example, the reservoir 102 of the storage assembly 101 and the pump 104 may be integrated with one another in some embodiments. However, in the preferred embodiment, the cap 118 of manual dispensing assembly 103 reversibly engages the reservoir opening 112 of the storage assembly 101 such that a user may disengage the cap 118 and reservoir opening 112 in order to depressurize the system during use or when filling the reservoir 102. Whether the reservoir 102 and storage assembly 101 are integrated or separable, the cap 118 of the dispensing assembly 103 and the reservoir opening 112 of the storage assembly 101 form a leakproof seal. The leakproof seal is designed to promote safe storage and handling of the nutritional substance, while still providing ease of operation for those with limited dexterity.

In one embodiment, the feeding system 100 utilizes two reservoirs 102, the first reservoir containing nutritional substance and the second reservoir containing a second liquid substance such that less frequent disconnection and cleaning of the feeding system 100 elements is required. In addition, one reservoir may be changed out while the other reservoir maintains a continual feeding. This arrangement results in larger feeding volumes and a reduced risk of contamination in the feeding system 100. In other embodiments, the feeding system 100 with two reservoirs may both hold nutritional substance, medication, fluid refreshment, and the like. With respect to these and other substances delivered, self-delivery may be accomplished with only one hand. This is accomplished by setting the bottle on a desk or other flat surface and then pumping with one hand.

In one embodiment, a cupholder adapter (not shown) is utilized with the feeding system 100. Advantageously, the cupholder adapter holds the feeding system 100 in position during a feeding and during travel generally. In one embodiment, the cupholder adapter is adapted to sit upright in the cup holder of an vehicle during use. In another embodiment, the cupholder is adapted to sit upright in the center console of a vehicle that lacks cupholders. In other embodiments, in vehicles with two cup holders, a storage assembly 101 utilizing two reservoirs may pre-fill one reservoir with nutritional substance and pre-fill the other reservoir with water. Such a configuration frees the hands of the user to pump 104 the food as well as to rinse with water during use of the feeding system 100.

Preferably, the feeding system 100 and other parts of the system, such as the pump 104, are cleaned and prepared for a further use. If desired, the pump 104 may also be used to flush the feeding tube 106, reservoir 102, and other system components with water or another suitable cleaning or flushing agent. The separable arrangement of the pump 104 and reservoir 102 also advantageously allows the reservoir 102 to be stored (e.g., refrigerated) and cleaned separately from the pump 104. For example, the spring 122, steel balls 302 and 304 (see FIG. 10), housing 120, and dip tube 124 may be easily removed from the reservoir 102, separated 102, and cleaned for reuse. Further, the relatively simple shape of the actuator 114, delivery tube 116, and cap 118 makes the pump 104 easy to clean. In some embodiments, the feeding system 100 is cleaned when water is pumped through the pump 104 simply by disconnecting the pump 104 from the reservoir 102 and reconnecting the pump 104 to a separate bottle of water. The tubing described herein has an inner diameter necessary to keep bubbles from forming. In one embodiment, the tubing is crack-resistant polyethylene tubing with an inner diameter of 0.17" and an outer diameter of 0.25". In other embodiments the inner diameter is between 0.15" and 0.20", and in still further embodiments the inner diameter is between 0.10" and 0.25", and the outer diameter is greater than 0.25".

In other embodiments, rather than cleaning a pump 104 for reuse, the pump 104 may also be discarded and replaced with a different pump 104 for the next use. The embodiments of the storage assembly 101 described herein, and obvious variants thereof, are well-suited to permit mixing of a nutritional substance within the storage assembly 101. Advantageously, the nutritional substance may be mixed, if necessary, after being added to the feeding device. For example, nutritional substance may be provided to the reservoir 102 as a plurality of ingredients that are subsequently mixed with one another in the storage chamber after mixing the plurality of ingredients.

The ingredients of a given nutritional substance may be mixed in the storage assembly 101, for example, by shaking the storage assembly 101. The option to mix the nutritional substance directly in the storage assembly 101 provides an advantage over the existing devices, systems and methods of enteral feeding, which typically use a bag for holding the nutritional substance. As discussed above, syringes are also unsuitable for mixing. When using a syringe, the nutritional substance typically is mixed in one reservoir 102 and then drawn into the syringe. In some embodiments, nutritional substance is pre-mixed before adding the nutritional substance to the reservoir 102. In other embodiments, nutritional substance is provided to the reservoir 102 as a plurality of ingredients that are subsequently mixed with one another in the storage assembly 101 after mixing the plurality of ingredients.

In preparing the feeding device, the storage assembly 101 may be coupled to the pump 104 and the extension set 137. The user may also desire to prime the system to remove a portion or all of the air from the system. Because the nutritional substance is delivered to the GI system (as opposed to intravenously, for example), some amount of air can be tolerated. The user may actuate the pump 104 to prime the feeding system 100, if desired. Other suitable methods of removing air from the feeding system may also be used, such as filling the reservoir 102 via the one-way port 148, as described below. Once primed, the extension set 137 may be connected to the actuator outlet 128.

Nutritional substance may be stored in the storage chamber before or after mixing. As mentioned above, various configurations of the storage assembly 101 permit convenient and sanitary storage of all feeding system 100 components, including the storage assembly 101 and the manual dispensing assembly 103. For example, as mentioned above, the one-way port 148 reversibly attaches to the second end of a feeding tube 138 when the feeding system 100 is not in use. This ensures sanitary storage of the feeding system 100. Further, as described above, adapter caps may be utilized in various configurations to promote efficacious and sterile storage of the feeding system 100.

In one embodiment of the invention, flowable nutritional substance is filled into the reservoir 102 through the reservoir opening 112. In another embodiment, the reservoir 102 is filled through the one-way port 148 of the dispensing assembly 103. If nutritional substance is filled via the reservoir opening, nutritional substance is added to the reservoir prior to securing the cap 118 to the reservoir 102. If nutritional substance is filled via the one-way port 148 of the storage assembly 101, nutritional substance is added to the reservoir 102 only after the cap 118 is secured to the reservoir opening. As described, the cap 118, port 148, and reservoir opening are sealed to create an enclosed reservoir 130 capable of receiving pressurizing nutritional substance.

In order achieve a dispensing stroke, the user actuates the pump 104 by depressing the actuator head 115 of the pump 104 using a downward force. The pump 104 of the preferred embodiment described above is manually-actuated and utilizes energy provided by the user to pressurize the reservoir 102. However, as discussed above, the pump 104 is not necessarily manually-actuated. For example, other types of mechanical, electric pumps, and other suitable pumps, may also be used.

Pressure generated by the actuation of the pump 104 pressurizes the reservoir 102. Pressure in the reservoir 102, when sufficient, tends to expel the nutritional substance from the reservoir 102 to the feeding tube 106 and ultimately to the patient. As illustrated in FIG. 1A, nutritional substance is delivered to the patient via the extension set 137.

It should be noted that the actuation of the pump 104, at least initially, may not sufficiently pressurize the reservoir 102 to cause the nutritional substance to reach the user, especially for new users that are unfamiliar with the feeding device. Thus, actuation of the pump 104 may be repeated until the storage assembly 101 is sufficiently pressurized. Once familiar with the feeding device, it is likely that the user will actuate the pump sufficiently to cause delivery of at least some portion of the nutritional substance to the patient.

In operation, the user monitors the delivery feed rate and determines if or when to actuate the pump 104 to maintain or increase the delivery feed rate of the nutritional substance. Notably, "feed rate" and "flow rate" are used interchangeably herein. Monitoring of the delivery feed rate may be accomplished by the sensory or physiological response resulting from the delivery of the nutritional substance to the GI system. In addition, or in the alternative, monitoring may be done visually, or by any other suitable method. "Monitoring" of the delivery feed rate may be as simple as determining if any nutritional substance is being delivered at any particular point in time. That is, it is not necessary that the user know the actual feed rate. If desired, however, suitable flow meters may be used to determine the feed rate and/or flow restrictors may be used to limit the maximum feed rate. As noted above, the monitoring (and actuation of the pump) may be done by the recipient of the nutritional substance, by one or more helpers, or any combination thereof.

In the preferred embodiment, the monitoring and dispensing of additional nutritional substance may be repeated substantially as described above. This process loop may be continued until the supply of the nutritional substance within the storage chamber 101 is exhausted, or at any time prior. Furthermore, at any point within the feeding process, the user can stop the flow of the nutritional substance, such as through applying a female adapter end cap 146 to the adapter 110 of the extension set, for example. The flow can then be restarted when desired. Alternately, the feeding system 100 may be stored for future use via any one of the several "stowed" arrangements as described above in part. If sufficient pressure remains within the reservoir 102, delivery of nutritional substance may continue. In other embodiments, the feeding system 100 may employ flow control devices, such as a fixed or variable flow regulator at any suitable location within the system. In some embodiments, the use of a flow restrictor can increase the duration of delivery of the nutritional substance for a given pressure.

Figure 7:
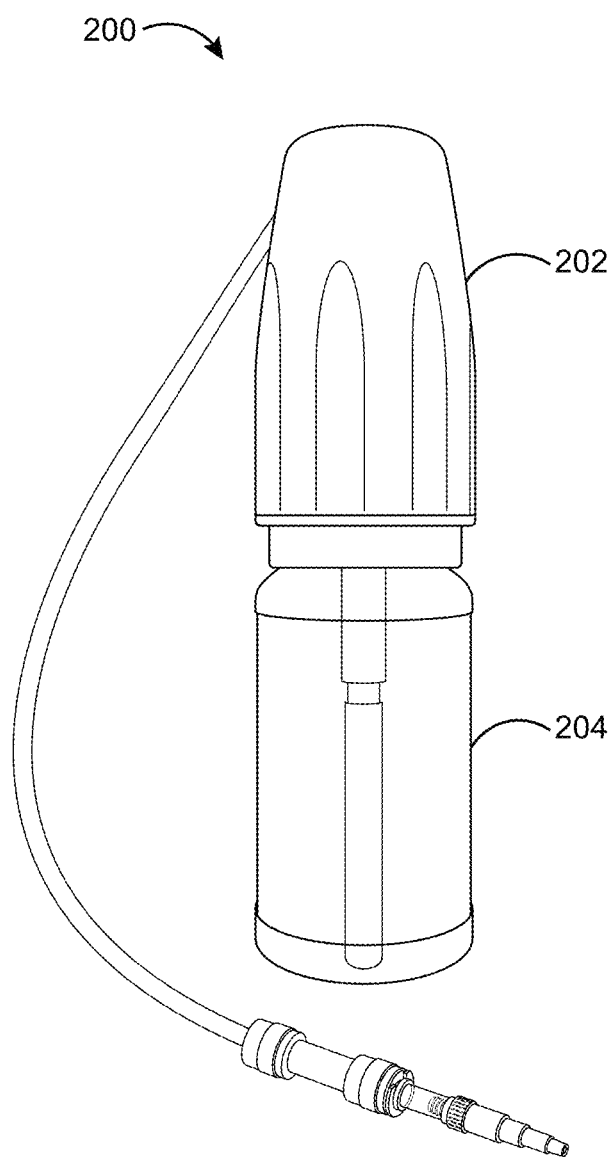
FIG. 7 illustrates a perspective view of a feeding system utilizing a rechargeable electric pump in accordance with one embodiment of the present invention.

In one embodiment of the feeding system 100, a rechargeable electric feeding system 200 is employed as shown in FIG. 7. As shown in FIG. 7, the rechargeable electric feeding system comprises an electric pump 202 positioned in a reservoir of the rechargeable electric pump 204. Alternately, the electric pump 202 may screw onto the top of the reservoir of the rechargeable electric pump 204. In some embodiments, the electric pump 202 is rechargeable, conveniently sized, and may automatically pump nutritional substance to the patient in various configurations. As shown in FIG. 7, the illustrated electric pump may be optionally powered by one or more batteries. In other embodiments, AC powered pumps, plug-in type pumps, and the like may also be used. The electric pump 202 may be of any suitable design that is capable of delivering a pressurizing nutritional substance, to the feeding tube 106 of a patient a suitable rate. In some embodiments, the electric pump 202 may include a user switch. The user switch may be a toggle-type switch that turns the electric pump on and off with successive engagements of the switch. Alternatively, the switch may simply comprise a button such that the electric pump is turned on when the button is depressed and turned off when the button is released. As will be apparent to one of skill in the art, other types of switches, controls, actuators or user inputs may be utilized to control the electric pump as desired. For example, a control that permits variable flow rates of the electric pump to be achieved may be desirable. In some arrangements, a controller, such as a microprocessor, may be incorporated into the electric pump 202 such that the controller may be programmed to carry out a feeding protocol. For example, such a pump could be programmed for extended term feeding, such as overnight feedings, in a manner similar to programmable peristaltic pumps that are currently available.

Figure 8:
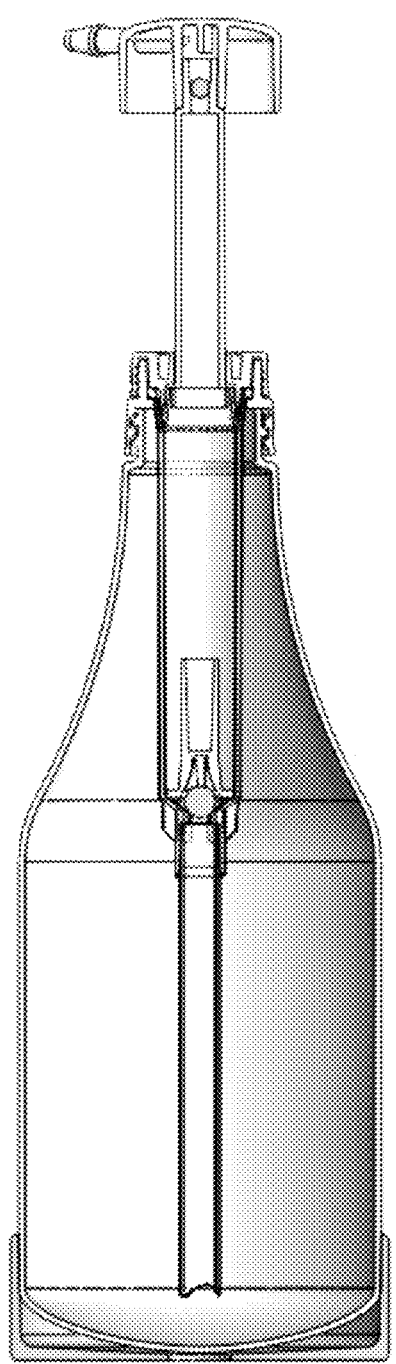
FIG. 8 illustrates an alternative embodiment of the invention wherein the pump has a flat bottom externally but a concave bottom internally.
Figure 9:
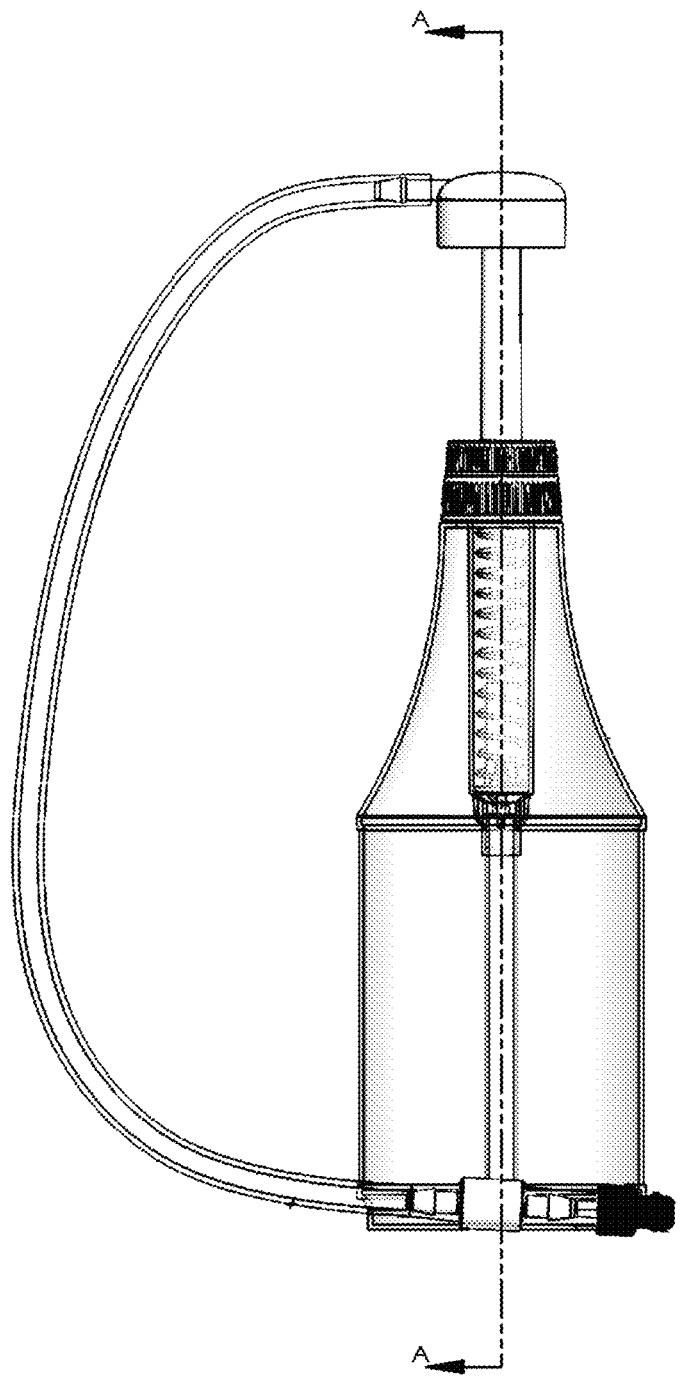
FIG. 9 illustrates an alternative embodiment of the invention showing the pipe in side view and with a cutline A-A.
Figure 10:
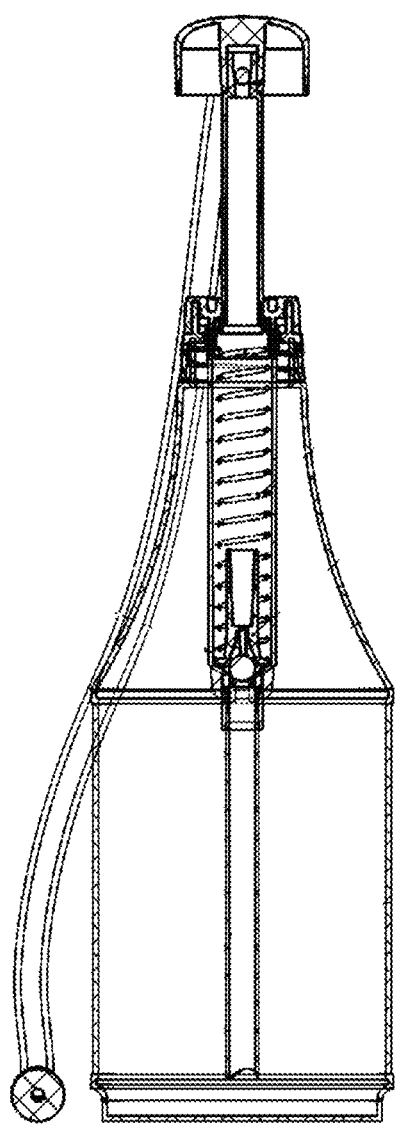
FIG. 10 illustrates an alternative embodiment of the invention showing a cross sectional view taken along cutline A-A in FIG. 9.
Figures 11, 12:
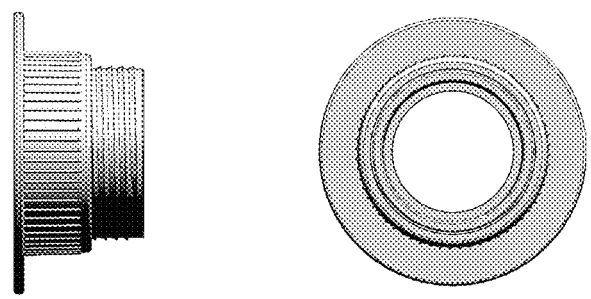
FIG. 11 is a side view of a uniquely threaded sealing cap adapter according to alternative embodiment of the invention.
FIG. 12 is a top view of a uniquely threaded sealing cap adapter according to alternative embodiment of the invention.
Figure 13:
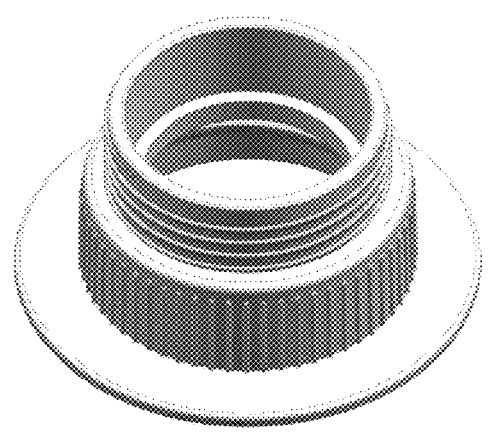
FIG. 13 is a first perspective view of a uniquely threaded sealing cap adapter according to alternative embodiment of the invention.
Figure 14:
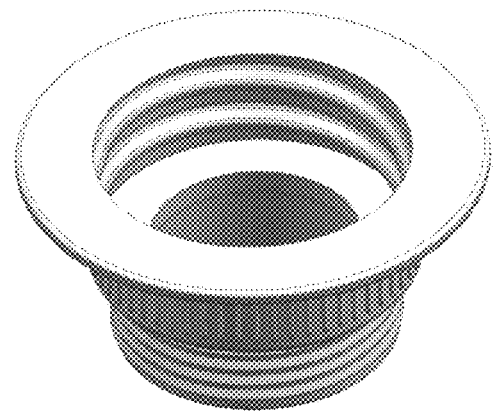
FIG. 14 is a first perspective view of a uniquely threaded sealing cap adapter according to alternative embodiment of the invention.
Figure 15:
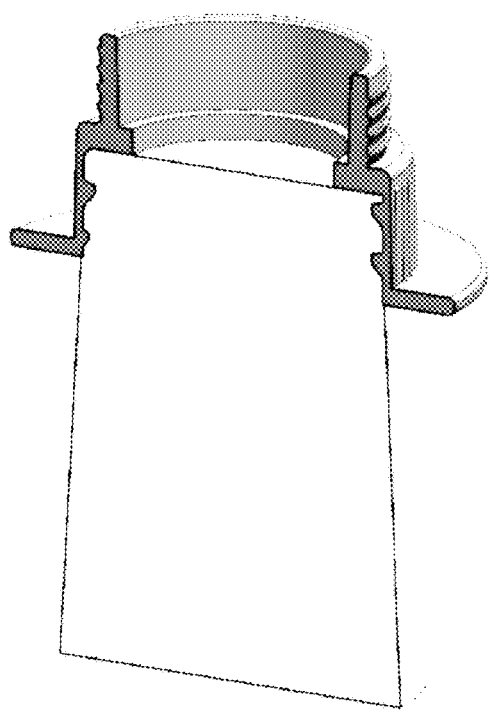
FIG. 15 is cutaway view of a threaded cap adapter engaged with the top of a bottle according to the alternative embodiment of the invention.

FIGS. 8-10 show additional embodiments. In FIG. 8 a cross sectional or cutaway view is shown wherein the system comprises a flat bottom externally, but a concave interior bottom. FIG. 9 shows an embodiment wherein a cutline A-A is taken and shown as cross sectional FIG. 10. FIGS. 11-15 depict various images of a cap adapter that serves as an intermediate between bottle and cap. The thread adapter has a first set of threads on its upper portion and a second set of threads on its lower portion. The sets of threads are different, with the first set being adapter to attach to a bottle cap and the second set being adapted to attach to a bottle.

In one embodiment, the method for delivering a flowable nutritional substance to a feeding tube comprises applying a manual force to an actuator of a pump; pressurizing a reservoir in response to energy originating from the application of the manual force to the pump; expelling the flowable nutritional substance from an actuator outlet in response to the pressure in the reservoir; and delivering the expelled flowable nutritional substance to the feeding tube.

In some instances, the manual force is applied at a user-selected magnitude and frequency such that a rate of the delivery of the flowable nutritional substance generally corresponds to the user's desired rate of consumption. In other embodiments at least a portion of the application of the manual force occurs during the delivery of the expelled nutritional substance. In some embodiments the method includes inserting a one-way valve into an outer wall of the reservoir to permit filling of pressurizing nutritional substance into the reservoir. In some embodiments the method includes securing a cap to the reservoir opening of the reservoir to form an enclosed reservoir. In some embodiments the method includes adding the nutritional substance to the storage assembly prior to securing the cap to the reservoir. In some embodiments the pump is capable of being coupled to the reservoir, the method further comprising coupling the pump and the reservoir prior to applying the manual force to the pump. In some embodiments the flowable nutritional substance is provided to the storage assembly as a plurality of ingredients that are subsequently mixed with one another in the storage chamber.

Although this invention has been disclosed in the context of certain preferred embodiments and examples, it will be understood by those skilled in the art that the present invention extends beyond the specifically disclosed embodiments to other alternative embodiments and/or uses of the invention and obvious modifications and equivalents thereof. In particular, while the present feeding system 100 for medical patients has been described in the context of particularly preferred embodiments, the skilled artisan will appreciate, in view of the present disclosure, that certain advantages, features and aspects of the system may be realized in a variety of other applications, such as the delivery of other types of flowable substances. Additionally, it is contemplated that various aspects and features of the invention described can be practiced separately, combined together, or substituted for one another, and that a variety of combination and subcombinations of the features and aspects can be made and continue to fall within the scope of the invention. Thus, it is intended that the scope of the present invention herein disclosed should not be limited by the particular disclosed embodiments described above, but should be determined only by a fair reading of the claims.

The foregoing description of the preferred embodiment of the present invention has been presented for the purpose of illustration and description. It is not intended to be exhaustive or to limit the invention to the precise form disclosed. Many modifications and variations are possible in light of the above teachings. In particular, while the present feeding system 100 for medical patients has been described in the context of particularly preferred embodiments, the skilled artisan will appreciate, in view of the present disclosure, that certain advantages, features and aspects of the system may be realized in a variety of other applications, such as the delivery of other types of flowable substances. Additionally, it is contemplated that various aspects and features of the invention described can be practiced separately, combined together, or substituted for one another. Thus, it is intended that the scope of the present invention not be limited by this detailed description, but by the claims and the equivalents to the claims appended hereto.

The invention claimed is:

1. A feeding system for delivering a flowable nutritional substance to a feeding tube, comprising:
    a body member comprising a reservoir, the reservoir having a delivery end and an outer wall, the outer wall incorporating a one-way port that permits a pressurizing nutritional substance to enter the reservoir, the one way port further comprising a valve;
    a cap that is securable to a reservoir opening of the reservoir, the cap and the reservoir opening configured to create an enclosed reservoir; and
    a pump operatively attached to the body member, wherein the pump is configured to pressurize the reservoir and a chamber within the reservoir, wherein the pump is further configured to pump nutritional substance out of the enclosed reservoir to cause said nutritional substance to be expelled from the enclosed reservoir;
    wherein the body member further comprises a spring assembly and a dip tube;
    wherein a screw connector and graduated tip are used to connect to the one-way port; and
    wherein a check valve is appropriately positioned to prevent the flow of the nutritional substance from a patient back into the feeding tube.

2. The system of claim 1, wherein the actuator comprises an actuator head that is depressed in response to a user applying a downward force on the actuator head, moving the actuator unit from a first position to a second position during a dispensing stroke, said actuator further being operatively engaged to draw said nutritional substance from the reservoir to the feeding tube through an outlet during a dispensing stroke.

3. An assembly for delivering a flowable nutritional substance to a patient, comprising:
    a storage assembly with a body member, the body member having a reservoir with a delivery end, a bottom end, and an outer wall, wherein the bottom end of the reservoir is substantially closed and is substantially flat, the outer wall incorporating a one way port that permits a pressurizing nutritional substance to enter the reservoir, the one way port further comprising a valve;
    a cap that is securable to a reservoir opening of the reservoir, the cap and said reservoir opening configured to create an enclosed reservoir and wherein the cap is widened to create a finger perch around which the user may hook his or her fingers to provide support;
    a manual dispensing assembly, the manual dispensing assembly comprising a pump with an actuator head and an actuator outlet, the actuator head being depressed in response to a user applying a downward force on the actuator head during a dispensing stroke;
    a feeding tube having a first end and a second end, the first end being attached to the actuator outlet;
    a check valve unit connected to the second end of the feeding tube, wherein the check valve unit comprises a one-way check valve and a check valve connection point, the one-way check valve allowing the flow of said nutritional substance in only one direction;
    an adapter unit operatively attached to the check valve unit, the adapter unit connecting to a feed tube port attached to the patient's abdomen to allow the passage of said nutritional substance;
    wherein the pump is configured to pump the nutritional substance from the reservoir and the check valve unit prevents the at least one food item from returning out from the patient; and
    wherein the check valve is appropriately positioned to prevent the flow of the nutritional substance from a patient back into the feeding tube.

4. The system of claim 3, wherein the port on the outer wall of the reservoir is adapted to reversibly attach to the second end of the feeding tube in order to stow the feeding tube when it is not in use, and wherein the assembly further comprises a housing with a spring assembly and a dip tube wherein the dip tube has a proximal end and a distal end, the proximal end attached to the spring assembly, the distal end configured to act as an inlet of the pump.

5. The feeding system of claim 3, wherein the adapter unit is used in combination with a female adapter end cap.

6. The feeding system of claim 3, wherein the storage assembly further comprises a cupholder element adapted to sit upright in the cup holder of a vehicle during use, wherein the feeding tube comprises crack-resistant polyethylene tubing with an inner diameter and an outer diameter.

7. The feeding system of claim 5, wherein a screw connector and graduated tip are used for the connection to the port on the outer wall of the reservoir.

* * * * *